United States Patent
Blanchard et al.

(10) Patent No.: US 11,382,891 B2
(45) Date of Patent: *Jul. 12, 2022

(54) PLANT PHENOLS AND THEIR USE IN THE TREATMENT OR PREVENTION OF EOSINOPHILIC ESOPHAGITIS

(71) Applicant: Société des Produits Nestlé S.A., Vevey (CH)

(72) Inventors: Carine Blanchard, Le Mont-sur-lausanne (CH); Sebastien Holvoet, Oron-la-Ville (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/732,914

(22) Filed: Jan. 2, 2020

(65) Prior Publication Data

US 2020/0222363 A1    Jul. 16, 2020

Related U.S. Application Data

(63) Continuation of application No. 14/429,147, filed as application No. PCT/EP2013/069668 on Sep. 23, 2013, now Pat. No. 10,548,873.

(30) Foreign Application Priority Data

Sep. 21, 2012  (EP) .................................... 12185377

(51) Int. Cl.
*A61K 31/366* (2006.01)
*A61K 31/216* (2006.01)
(Continued)

(52) U.S. Cl.
CPC .............. *A61K 31/366* (2013.01); *A23C 9/12* (2013.01); *A23C 9/123* (2013.01); *A23L 2/02* (2013.01); *A23L 2/38* (2013.01); *A23L 2/52* (2013.01); *A23L 7/126* (2016.08); *A23L 33/105* (2016.08); *A23L 33/40* (2016.08); *A23P 10/40* (2016.08); *A61K 31/216* (2013.01);
(Continued)

(58) Field of Classification Search
CPC .... A61K 31/366; A61K 31/216; A61K 36/53; A23L 33/105; A61P 1/04; A61P 37/08
See application file for complete search history.

(56) References Cited

U.S. PATENT DOCUMENTS

2010/0172941 A1*  7/2010  Vajdy ..................... A61K 39/12
                                                                 424/283.1
2010/0297230 A1  11/2010  Fletcher
2011/0160136 A1   6/2011  Offord Cavin et al.

FOREIGN PATENT DOCUMENTS

CN         1875996 A      12/2006
CN         102058532       5/2011
(Continued)

OTHER PUBLICATIONS

Zheng, "Development of Active Ingredients in Plants", Jun. 30, 2005, p. 94.
(Continued)

*Primary Examiner* — Timothy P Thomas
(74) *Attorney, Agent, or Firm* — K&L Gates LLP

(57) ABSTRACT

Plant phenols, in particular, plant phenolic acids, like rosemarinic acid, ellagic acid, and chlorogenic acid, can be used in the treatment or prevention of eosinophilic esophagitis.

18 Claims, 2 Drawing Sheets

(51) Int. Cl.
| | |
|---|---|
| A61K 36/53 | (2006.01) |
| A23L 33/105 | (2016.01) |
| A61K 36/185 | (2006.01) |
| A61K 36/74 | (2006.01) |
| A23L 33/00 | (2016.01) |
| A23L 7/126 | (2016.01) |
| A23P 10/40 | (2016.01) |
| A23C 9/12 | (2006.01) |
| A23C 9/123 | (2006.01) |
| A23L 2/02 | (2006.01) |
| A23L 2/38 | (2021.01) |
| A23L 2/52 | (2006.01) |

(52) U.S. Cl.
CPC .......... *A61K 36/185* (2013.01); *A61K 36/53* (2013.01); *A61K 36/74* (2013.01); *A23V 2002/00* (2013.01)

(56) References Cited

FOREIGN PATENT DOCUMENTS

| | | |
|---|---|---|
| CN | 102453038 A | 5/2012 |
| JP | H05310745 | 11/1993 |
| JP | H08333267 | 12/1996 |
| JP | H09110710 | 4/1997 |
| JP | 2002080360 | 3/2002 |
| JP | 2004010488 | 1/2004 |
| JP | 2005082497 | 3/2005 |
| JP | 2005089304 | 4/2005 |
| JP | H2005179285 | 7/2005 |
| JP | 2008273979 | 11/2008 |
| JP | 2011057562 | 3/2011 |
| WO | 2007129406 | 11/2007 |
| WO | 2009016018 | 2/2009 |
| WO | 2010106495 | 9/2010 |
| WO | 2012105798 | 8/2012 |
| WO | 2012178118 | 12/2012 |

OTHER PUBLICATIONS

Zhu, "Leymus Chinensis Biological Ecology", Oct. 31, 2004, p. 535.
Zhang, "The Site-Specific Accumulation of Polyphenol Ellagic Acid in the Epithelial Tissue of the Digestive Tract, the Ellagic Acid is Useful for Prevention of Cancer in the Diet", World Phytomedicines, vol. 22, Issue No. 6, Nov. 30, 2007, p. 268.
Tanaka et al., "Inhibition of 4-Nitroquinoline-I-Oxide-Induced Rat Tongue Carcinogenesis by the Naturally Occurring Plant Phenolics Caffeic, Ellagic, Chlorogenic and Ferulic Acids", Carcinogenesis, vol. 14, Issue No. 7, 1993, pp. 1321-1325.
China Patent Office Action Received for Application No. 201910603651. 2, dated Feb. 20, 2021, 14 Pages.
Examination Report issued in related Australian Patent Application No. 2013320148 dated Apr. 28, 2017.
Office Action issued in related Japanese Patent Application No. P2015-532433 dated Jun. 6, 2017.
Straumann, Alex, et al. "Anti-interleukin-5 antibody treatment (mepolizumab) in active eosinophilic oesophagitis: a randomized, placebo-controlled, double-blind trial." Gut (2009): 21-30. Downloaded from http://gut.bmj.com/ on Apr. 20, 2017.
Stein, Miguel L., et al. "Anti-IL-5 (mepolizumab) therapy for eosinophilic esophagitis." Journal of Allergy and Clinical Immunology 118.6 (2006): 1312-1319.
Rogerio, Alexandre P., et al. "Anti-inflammatory effects of Lafoensia pacari and ellagic acid in a murine model of asthma." European Journal of Pharmacology 580.1 (2008): 262-270.
Kim, Hye-Rin, et al. "Chlorogenic acid suppresses pulmonary eosinophilia, IgE production, and Th2-type cytokine production in an ovalbumin-induced allergic asthma: activation of STAT-6 and JNK is inhibited by chlorogenic acid." International immunopharmacology 10.10 (2010): 1242-1248.
Straumann et al. "Pediatric and adult eosinophilic esophagitis: similarities and differences" Allergy, vol. 67, 2012, pp. 477-490, Pub Year: 2012.
Zuzak et al.; "Accidental intakes of remedies from complementary and alternative medicine in children-analysis of data from the Swiss Toxicological Information Centre"; Eur. J. Pediatr.; 169: 681-688, Pub Year: 2010.
Rogerio et al.; "The activity of medicinal plants and secondary metabolites on eosinophilic inflammation", Pharmacological Research; 62: 298-307, Pub Year: 2010.
Lee et al. (WO 2012/105798 A2); English translation provided by Google Patents on Jul. 11, 2016; http://www.google.com/patents/WO2012105798A2?cl=en.
Farah et al.; "Chlorogenic Acids from Green Coffee Extract are Highly Bioavailable in Humans"; 2008; J. Nutr.; 138: 2309-2315.
Straumann et al.; "Pediatric and adult eosinophilic esophagitis: similarities and differences"; Apr. 2012; Allergy; 67: 477-490.
Singh et al.; "Dietary polyp he no is in the prevention and treatment of allergic diseases"; 2011; Clinical & Experimental Allergy; 1-14.
Sanbongi et al.; "Rosmarinic acid in perilla extract inhibits allergic inflammation induced by mite allergen, in a mouse model"; 2004; Clin. Exp. Allergy; 34: 971-977.
MeSH Browser Descriptor of eosinophilic esophagitis; https://meshb.nlm.nih.gov/#/record/ui?ui=D057765; accessed Dec. 20, 2016.

* cited by examiner

PLANT PHENOLS AND THEIR USE IN THE TREATMENT OR PREVENTION OF EOSINOPHILIC ESOPHAGITIS

PRIORITY CLAIMS

The present application is a Continuation of U.S. patent application Ser. No. 14/429,147 filed Mar. 18, 2015, which is a National Stage of International Application No. PCT/EP2013/069668 filed Sep. 23, 2013, which claims priority to European Patent Application No. 12185377.4 filed Sep. 21, 2012, the entire contents of which are incorporated herein by reference.

FIELD OF INVENTION

The present invention relates to the use of plant phenols for use in the treatment or prevention of eosinophilic esophagitis.

BACKGROUND

Eosinophilic esophagitis is an inflammatory condition of the esophagus that can be triggered or not by an antigen. Symptoms include functional abdominal pain, vomiting, difficultly to thrive, swallowing difficulty, food impaction, and heartburn. The disease was initially described in children but occurs in adults as well. Eosinophils can usually not be found in normal esophageal mucosa. However, in eosinophilic esophagitis the eosinophils infiltrate the epithelium of the esophagus and can often be found in clusters close to the surface of the epithelium. Frequently the infiltration of the eosinophils is associated with a thickening of the basal layer as a reaction to the inflammatory activities in the epithelium.

There are different strategies available for the treatment of eosinophilic esophagitis including medical therapy, mechanical dilatation, and modification of the diet.

In medical therapy corticosteroids and proton pump inhibitors have been found to mitigate the symptoms. It has also been observed that the allergic response can be reduced by the administration of antihistamines. Mechanical dilatation of the esophagus might be considered in severe cases where the swelling of the epithelium is threatening to block the esophagus.

Previous nutritional treatment regimens mainly aim at a dietary modification by excluding potential food allergens from the diet. Thus, an allergy evaluation is performed and thereby those allergens are identified which might be inducing the disease. Subsequently, the diet is modified to exclude the identified allergen. Other approaches aim at the provision of a complete nutrition lacking any potential allergens. For example, US 2008/0031814 describes a nutritional composition lacking allergenic ingredients and thereby preventing the development of allergic inflammatory conditions. Thus, instead of treating the disease by the choice of certain nutritional ingredients the diets of the prior art aim at avoiding allergenic ingredients in the diet.

Therefore, there is a need for a composition comprising natural compounds that does not only lacks main allergens but can actively prevent or treat eosinophilic esophagitis.

SUMMARY

It is the object of the invention to provide new and alternative solutions to the problem of preventing or treating eosinophilic esophagitis. It has been surprisingly found that plant phenols are useful in preventing or treating eosinophilic esophagitis. The evaluation of ingredients which are useful in the treatment or prevention of eosinophilic esophagitis is performed using an established mouse model for eosinophilic esophagitis (Akei et al., "Epicutaneous antigen exposure primes for experimental eosinophilic esophagitis in mice", Gastroenterology, 2005 September; 129(3):985-94). This model uses various parameters including the number of eosinophils in the esophagus as indicators for the effect on eosinophilic esophagitis. Accordingly, is ideally suited for the testing of compounds that are candidates for the treatment or prevention of eosinophilic esophagitis.

Therefore, the invention relates to a composition comprising plant phenols for use in the prevention or treatment of eosinophilic esophagitis. The phenols can be selected from the group consisting of rosmarinic acid, ellagic acid, punicalagins, cholorgenic acid, or mixtures thereof. The plant phenol can be a polyphenol or tannins. The plant phenols can be comprised in plant extracts and the composition can comprise said plant phenols. Thus, the invention also relates to a composition comprising plant extracts selected from the group consisting of extracts from thyme, pomegranate, green coffee, or mixtures thereof.

The composition can be administered orally, optionally by tube feeding or topical-orally. The composition can be administered to a human being or a pet animal, in particular a cat or a dog. The human being can be a young child between the age of 1 month and six years, an older child between the age of 6 to 18 years, or an adult person. Thus, the nutritional composition can be selected from the group consisting of an infant feeding composition, a follow-up formula, a growing-up milk, an infant cereal, or a baby nutritional composition. The composition can also be a nutritional composition, a pet nutritional composition, a oral nutritional supplement or a pharmaceutical product. In particular, the nutritional composition can be selected from the group consisting of a beverage product, a yoghurt product, fermented milk, a fruit juice, or a cereal bar. The nutritional composition can be a food for specific medical purposes such as a health care nutritional composition for oral feeding, a nutritional product for enteral feeding or a parenteral feeding product.

DEFINITIONS

Figure 1:
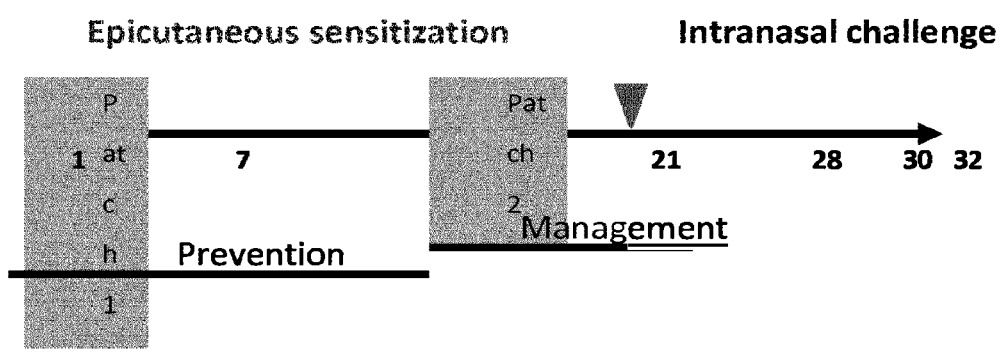
FIG. 1. Experimental protocol

"Eosinophilic esophagitis" is an inflammatory condition of the esophagus. Symptoms include functional abdominal pain, vomiting, difficultly to thrive, swallowing difficulty, food impaction, and heartburn. It is characterized by the presence of eosinophilic infiltrates in the epithelium of the esophagus. The infiltration of the eosinophils can be associated with a thickening of the basal layer. Under the ICD-9 (international classification of diseases revision 9) it is designated as 530.13. If more than 15 eosinophils per "high power filed" (defined below) are found in a mucosal biopsy of the esophagus the disease eosinophilic esophagitis can be considered as diagnosed.

"Plant phenols" are a class of natural organic compounds. They comprise one or more phenolic groups. Only phenols that occur in plants and artificially synthesized phenols that are identical to phenols naturally occurring in plants are considered here.

"Phenolic groups" are groups that comprise a phenyl group bonded to a hydroxyl group. The hydrogen of the ring carbons of the phenolic groups can be substituted with further residues (like hydroxyl-, alkan-, alken-residues, ring C formed as carboxyl etc.). A particular preferred substitution is a further hydroxyl group.

"Plant polyphenols" in the sense of the invention are phenols comprising more than 2 phenolic groups.

"High Power Field (HPF)" when used in relation to the invention refers to the area visible under the maximum magnification power of the objective of a microscope being used. This can represent a 400× magnification level.

"Topic-oral" when used in this invention is a form of administration where a composition is applied topically to the esophageal mucosa for direct adsorption of the composition by the esophageal mucosa. This form of administration is intended to avoid adsorption of the composition via the digestive tract starting after the esophagus. A typical form of topical-oral administration is the administration in form of spray that is sprayed via the oral cavity and then swallowed into the esophagus.

DETAILED DESCRIPTION

The section headings serve to clarify the subject matter and should not be interpreted to limit the subject matter. If ranges of values are disclosed each individual value is considered to be covered by the range, in particular, each integer number. If not noted otherwise, values in % relate to weight/weight (w/w) values. It has been surprisingly found that certain plant phenols are useful in decreasing the amount of eosinophils. This finding was made in a mice model for eosinophilic esophagitis. Therefore, it can be concluded that plant phenols can be used in the treatment or prevention of eosinophilic esophagitis which is a disease characterized by an increase of the number of eosinophils in certain tissues.

Compositions

The compositions of the invention can comprise several ingredients, the main active ingredient being plant phenols, which are explained in more detail below.

Plant Phenols

The composition comprises at least one plant phenol. Plant phenols comprise at least 1, 2, 3, 4, 5, or 6 phenolic residues. Particularly preferred are plant phenols comprising 1 or 2 phenolic residues. The plant phenols preferentially do merely consist of hydrogen, carbone, and oxygen. The plant phenols preferentially do comprise or consist of a residue selected from the group consisting of at least one cyclohexan residue, phenolic residue, H-residue, OH— residue, C=residue, CO2H— residue, ethyl residue, —O— residue.

The composition can comprise at least one, at least two, at least three, or at least four different plant phenols. It can be expected that a combination of plant phenols will show synergistic effects on eosinophilic esophagitis. The phenols are phenols that occur in natural plant sources. The natural sources can be thyme, pomegranate, or green coffee, or mixtures thereof. The phenols may be extracted from those natural sources by any known extraction technique, like an extraction with water or an organic solvent, like ethanol or ether.

The composition can comprise a plant extract comprising the plant phenols. The composition can comprise plant extracts selected from the group consisting of thyme, pomegranate, green coffee, or any possible combination or mixture thereof. In particular, the composition can comprise thyme, pomegranate and green coffee extract.

The plant extract can be thyme extract and comprise rosmarinic acid.

The plant extract can be pomegranate extract and comprise ellagic acid.

The plant extract can be green coffee and comprise cholorgenic acid.

The plant phenols can be phenolic acids. In particular, the plant phenols can be rosmarinic acid, methylated rosmarinic acid, coumaric acid, ferulic acid; ellagic acid, ellagitannins, punicalagins, gallic acid, gallotannin; cinnamic acids (like caffeic acid, ferulic acid and p-coumaric acid) and esthers of cinnamic acid with (−)-quinic acid, one preferred cinnamic acid esther is cholorgenic acid, derivates of cholorgenic acid like its 3-0-glucoside, 3-0-galactoside and 3-0-arabinoside are also considered. Phenols can also be flavonoids or catechins. It is also contemplated that any of the above described plant phenols can be excluded from the composition if this deems to be appropriate. In a particular embodiment epicatechin are excluded from the composition. Mixtures of these plant phenols are also contemplated. In particular, the mixture can comprise at least 1, 2, 3, 4, 5, 6, 7, 8, 9, 10, 11, 12 of the above described phenols. The composition can comprise any permutation of the above described phenols in the composition.

Each of the phenols or the sum of a combination of those phenols (or in the form of extracts) can be present in the composition or in a composition that has been reconstituted from powder or concentrated form, at a concentration of between 0.1% and 1%, between 0.15% and 0.8%, between 0.15% and 0.7%, between 0.15% and 0.6%, between 0.15% and 0.5%, between 0.2% and 0.4%, or be present at a concentration of 0.3%.

Particularly preferred phenols are rosmarinic acid, ellagic acid, and cholorgenic acid, or any possible combination or mixtures thereof.

Formulations

The above described compositions can be formulated in liquid or solid form. The liquid form can be formulated to be in a form suitable for spraying, that is, in the form of a spray. This can be achieved by connecting a compartment containing the composition to a spray nozzle. The liquid when transported through the spray nozzle is atomized allowing the obtained droplets to distribute evenly onto a surface. Various ways to transport a liquid through a spray nozzle are known to the skilled person. For example, the container containing the composition may be under pressure compared to the surrounding atmospheric air pressure. Alternatively, a pump mechanism may transport the spray through the nozzle. The use of a spray allows, for example, to spray the composition via the oral cavity into the esophagus and thereby bring the composition into direct contact with the esophageal mucosa. Subsequently, the composition can be absorbed by the mucosa and then achieve a systemic distribution within the body.

The compositions can further comprise at least one additional active agent, carrier, vehicle, excipient, or auxiliary agent identifiable by a person skilled in the art upon reading of the present disclosure.

The composition can be in the form of an oral nutritional supplement, a nutritional composition or pharmaceutical product. A nutritional composition, oral nutritional supplement or pharmaceutical product can comprise the composition or kit of the invention.

Nutritional Composition

As used herein, the term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplement. An oral supplemental nutritional composition contains mainly or exclusively the essential active ingredients of the claimed composition (the plant phenols) and can be consumed in addition to the regular nutrition of a patient.

A disease or condition specific nutritional composition is a composition that delivers nutrients or pharmaceuticals and can be a complete or partial nutritional composition.

A nutritional composition may additionally comprise the following nutrients and micronutrients: a source of proteins, a source of lipids, a source of carbohydrates, vitamins and minerals. The composition may also contain anti-oxidants, stabilizers (when provided in solid form) or emulgators (when provided in liquid form). In a preferred embodiment the composition is amino acid-based formula, that means, the only source of amino acids are free amino acids. Thus, in another embodiment, the nutritional composition further includes one or more amino acids. Non-limiting examples of amino acids include Alanine, Arginine, Asparagine, Aspartate, Citrulline, Cysteine, Glutamate, Glutamine, Glycine, Histidine, Hydroxyproline, Hydroxyserine, Hydroxytyrosine, Hydroxylysine, Isoleucine, Leucine, Lysine, Methionine, Phenylalanine, Proline, Serine, Taurine, Threonine, Tryptophan, Tyrosine, Valine, HICA (Alpha-Hydroxyisocaproic Acid), HIVA (Alpha-Hydroxyisovaleric Acid), HIMVA (alpha-hydroxymethylvaleric acid) or a combination thereof. In a preferred embodiment, non-limiting examples of amino acids include proline, hydroxyproline, hydroxytyrosine, hydroxylysine and hydroxyserine and combinations thereof.

In a further embodiment the nutritional composition may comprise minerals such as sodium, potassium, calcium, phosphorus, magnesium, chloride, iron, zinc, copper, manganese, fluoride, chromium, molybdenum, selenium, iodine or any combination thereof.

In a further embodiment the nutritional composition comprises further vitamins such as Vitamin A, Vitamin E, Vitamin C, Vitamin B1, Vitamin B2, Pantothenic Acid, Vitamin B6, Vitamin B12, Niacin, Folic Acid, Biotin and Choline or any combination thereof.

In one embodiment, the nutritional composition is selected from the group consisting of an infant feeding composition, a follow-up formula, a growing-up milk, an infant cereal, or a baby nutritional composition. These products are particularly well suited to address and solve the problem of the prevention or reduction of symptoms of eosinophilic esophagitis in babies and young children. However, other products like beverages and powders (sachet format) can also be chosen for older children and adults as described in the following.

In a further embodiment, the nutritional composition is selected from the group consisting of a beverage product, an amino acid based beverage, a yoghurt product, fermented milk, a fruit juice, a dried powder in sachet format or a cereal bar. These nutritional compositions are well suited for administering plant phenols to older children and adult humans. The nutritional compositions can well be enriched with plant phenols and have a credible image to provide a health oriented functional nutritional composition to the consumers.

A particular need for products to reduce symptoms of eosinophilic esophagitis may be in the clinical environment, such as in hospitals, clinics and homes for elderly persons. Therefore, in a still further embodiment, the nutritional composition is a food for specific medical purposes such as a health care nutritional composition for oral feeding, and/or a nutritional product for enteral or parental feeding. In the latter case it will only include ingredients which are suitable for parenteral feeding. Ingredients that are suitable for parental feeding are known to the person skilled in the art. In particular, a parental feeding composition will contain the plant phenols in pure or substantially pure form (i.e. usually not be provided in the form of plant extracts which are only enriched for the plant phenol) but the composition can also comprise other ingredients that are known to be suitable for parenteral nutrition. A further advantage of the invention is that plant phenol can be provided in relatively high local concentration and low volumes of a medical nutritional composition and hence be administered effectively to patients in such need.

Kits

The above compositions may also be provided as kits. In those kits the all or a part of the ingredients of the above described compositions are provided in a separate (i.e. not mixed) form. A kit of the invention can comprise the plant phenols on the one hand and all the remaining ingredients on the other hand in separate form. A kit of the invention can comprise at least two or three plant phenols provided in a separate form. In an alternative embodiment, the kits can comprise each of the ingredients of the above described composition in a separate form.

Therapeutical Uses and Methods

The composition or the kit of the invention can be used in the treatment or prevention of eosinophilic esophagitis or the reduction of the number of eosinophils, in particular, in the epithelium, in particular, in the epithelium of the esophagus. The composition or the kit of the invention can also be used in a method for the treatment or prevention of eosinophilic esophagitis or the reduction of the number of eosinophils, in particular, in the epithelium, in particular, in the epithelium of the esophagus.

A reduction in the number of eosinophils is defined as the reduction of eosinophils that are found in a high power field of a microscope in a mucosal biopsy of the esophagus below a value of 10-20, particularly 15 in human being that is suffering from eosinophilic esophagitis. Thus, a reduction in the sense of the invention is a significant reduction compared to a positive control in animal models. A reduction in the sense of the invention can be a reduction to values below 19, 18, 17, 16, 15, 14, 13, 12, 11, 10, 9, 8, 7, 6, 5, 4, 3, 2, 1 or to 0 in a high power field of a microscope in a mucosal biopsy of the human esophagus. Alternatively the reduction can be defined by reference to the number of eosinophils a subject suffering from eosinophilic esophagitis has or is expected to have if no preventive measures are taken using the composition of the invention. Thus, a reduction may be a percentage of reduction (of at least 50%, 60%, 70%, 80%, 90%, 95%, 99%, or 100%) in reference to a number of eosinophils found in a high power field of a microscope in a mucosal biopsy of the esophagus of an animal or human being that is suffering from eosinophilic esophagitis. Alternatively, a reduction in the sense of the invention may be a reduction in absolute numbers by 5, 6, 7, 8, 9, 10, 11, 12, 13, 14, 15, 16, 17, 18, 19, or 20 or more than 20 in reference to a number of eosinophils found in a high power field of a microscope in a mucosal biopsy of the esophagus of a human being that is suffering from eosinophilic esophagitis. The reference value can be in the range of 10-20, or be 15. The reduction may be observed after 5, 10, 15, 20, 25, 30, 60, 120 days of treatment.

The compositions and kits can be provided in a form that is suitable for oral or topical administration and then be administered accordingly. Administration can start before the symptoms of eosinophilic esophagitis occur in a subject, concurrently together with the appearance of the symptoms or after the symptoms have shown. Administration can be performed for 1, 20, 30, 60, 120, 360 days or longer. If the subject is a human, the subject to which the composition is administered, can be between the age of 4 months and 6 years, between the age of 6 years and 18 years, or be an adult person.

In an embodiment, the composition is intended for consumption by an animal, preferably a cat or a dog. Similarly as with humans, eosinophilic esophagitis can be observed in animals, in particular with domesticated animals and animals kept as pets. Advantageously, the current invention provides a liquid which can be provided to a companion animal by his owner.

The sum of plant phenols in the composition is administered to a human being in an amount preferably in the range from 3 mg/kg body weight per day to 100 mg/kg body weight per day, preferably 10 to 50 mg/kg body weight day. Preferably, the composition provides from about 25 mg to 10 g per day, from 50 mg to 10 g per day, preferably from 100 mg to 5 g per day, even more preferably from 300 mg to 1 g per day. These preferred doses allow to provide on one hand sufficient plant phenols to a relevant patient per day in order to provide the expected health benefit and on the other hand not to overdose plant phenols to prevent the risk of any potential undesirable or toxic effects to the patient.

Methods of Production

A method for producing the above described composition is provided and comprises providing at least one of the above described plant phenols, adding optionally at least one further ingredient, for example, selected from the group consisting of one or more amino acids, fat, or carbohydrate, adding optionally at least one nutrient or micronutrient, adding a carrier or/and water.

Those skilled in the art will understand that they can freely combine all features of the present invention disclosed herein. In particular, features described for different embodiments of the present invention may be combined. Further advantages and features of the present invention are apparent from the figures and examples.

EXAMPLES

Example 1: Effect of Plant Phenols on the Eosinophil Count 5-8 weeks old female Balb/c mice were sensitized by epicutaneous application of 200 µg of an allergic extract. A small part of the back of the mouse was shaved. A patch of sterile gauze (1×1 cm) with the allergen was secured to the skin with a bio-occlusive transparent dressing 2461 (Johnson and Johnson) and a Band-Aid. The patch remained on the skin for sensitization periods of 4 to 7 consecutive days till it felt or was removed at day 8. Few days after the last sensitization day (day 21 to 28) the mice were exposed on day 30 to an intranasal challenge (100 µg) in anesthetized mice and mice were harvested on day 32.

Aspergillus fumigatus antigen extract and house dust mite extract were obtained from Greer Laboratories, Lenoir, N.C. and were diluted to 100 µg/µL with normal saline.

Effect of plant phenols was tested using plant phenols extract in the food from 6% (w/w) thyme (5% rosmarinic acid), 1% (w/w) Pomegranate (30% ellagic acid) and 1% (w/w) green coffee (30% cholorgenic acid) from Monteloeder (Spain).

|         | Number of mice | Epicutaneous sensitization | Challenges | Treatment |
|---------|----------------|---------------------------|------------|-----------|
| Group A | 8              | 3X saline                 | 1x ASP     | none      |
| Group B | 8              | 3X ASP                    | 1x ASP     | none      |
| Group C | 8              | 3X ASP                    | 1x ASP     | Thyme     |
| Group D | 8              | 3X ASP                    | 1X ASP     | Pomegranate |
| Group E | 8              | 3X ASP                    | 1X ASP     | Green coffee |

Figure 2A:
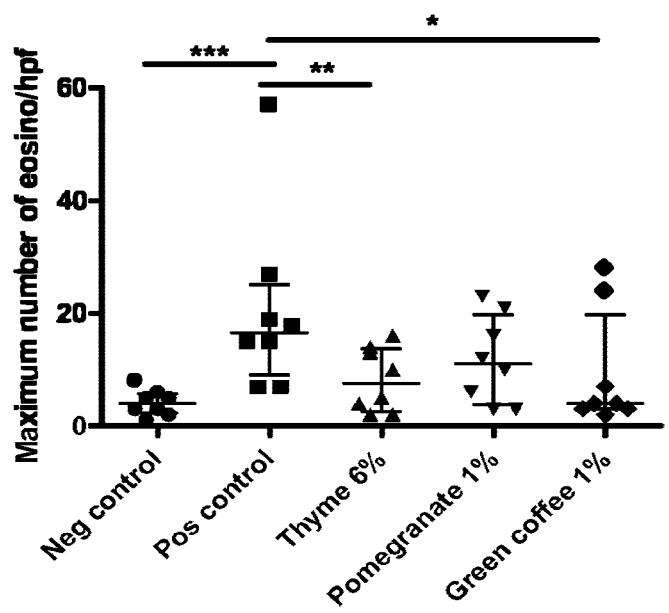
FIGS. 2A and B. Eosinophil number in the esophagus. The esophagea were harvested and tissue histology was performed. Eosinophils were identified and counted on Hematoxylin & Eosin (H&E) stained slides per high powered field (hpf). The maximal number of eosinophils found in one hpf field in the whole esophagus is shown in A. The maximal number of eosinophils present in the esophagal epithelium is represented in B.
Figure 2B:
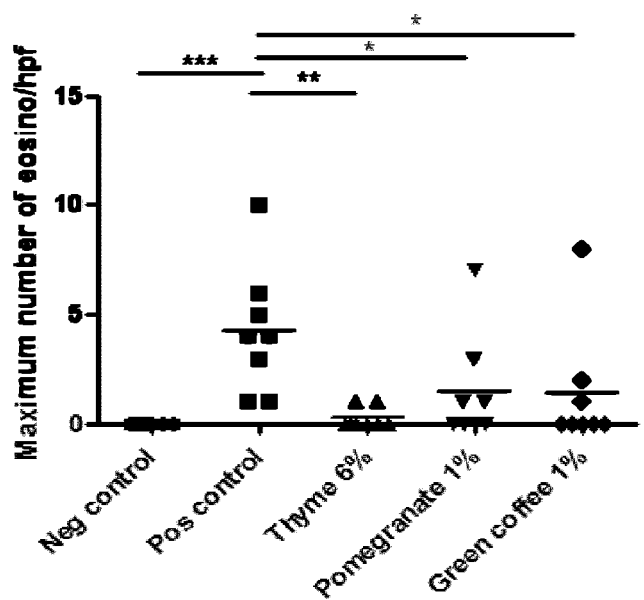

Esophagi were harvest and stained with hematoxylin eosin and eosinophils were counted (maximum/high power field, see FIG. 2).

Compared to the positive control a signification reduction of eosinophils in the esophagus has been observed with thyme and coffee polyphenol in the esophagus and with all plant extract in the esophageal epithelium. This is suggestive of a broader effect of plant derived phenols in the reduction of the eosinophilic load induced by allergens.

Example 2: Clinical Trial

Seven cohorts of 20-30 people in the age of 18-60 suffering from eosinophilic esophagitis as indicated by the presence of more than 15 eosinophils per high power field in a mucosal biopsy obtained during esophagogastroduodenoscopy receive an amino acid based composition VIVONEX® PEDIATRIC further containing extracts as indicated in the table below.

At standard dilution, VIVONEX® PEDIATRIC is a 0.8 kcal/ml formula having by % of kcal: 12% protein (free amino acids); 63% carbohydrate and 25% fat. A MCT:LCT Ratio of 70:30; n6:n3 Ratio of 7.7:1; Osmolality (mOsm/kg water) of 360; free water of 89%; it meets or exceeds 100% DRIB for protein and 25 key vitamins and minerals; supplemental Glutamine: 3.0 g/L; Supplemental L-Arginine: 2.0 g/L The thyme extracts contains 5% of the plant phenol rosmarinic acid, the pomegranate extract contains 30% of the plant phenol ellagic acid and 1% the green coffee 30% of the plant phenol cholorgenic acid (Monteloeder, Spain).

|         | Number of subjects | Agent(s) |
|---------|--------------------|----------|
| Group A | 15                 | Water    |
| Group B | 15                 | 6% thyme extract |
| Group C | 15                 | 1% Pomegranate extract |
| Group D | 15                 | 1% Green coffee extract |

-continued

| | Number of subjects | Agent(s) |
|---|---|---|
| Group E | 15 | 2.5% Thyme extract, 0.5% Pomegranate extract |
| Group F | 15 | 2% Thyme extract, 0.3% Pomegranate extract, 0.3% green coffee extract |

The subjects receive the extracts in such an amount that 500 mg of the respective plant phenol(s) are administered daily. The number of eosinophils is determined as the number of eosinophiles visible in the high power field of a mucosal biopsy obtained during esophagogastroduodenoscopy at day 15 and 30 after start of the study. Known associated symptoms like swallowing difficulty, food impaction, and heartburn are also observed in the study.

The invention is claimed as follows:

1. A method for treatment of eosinophilic esophagitis in an individual in need thereof, the method comprising administering to the individual a composition comprising a plant phenol selected from the group consisting of rosmarinic acid, ellagic acid, chlorogenic acid, and mixtures thereof.

2. The method of claim 1, wherein the composition comprises a plant extract that provides at least a portion of the plant phenol.

3. A method for treatment of eosinophilic esophagitis in an individual in need thereof, the method comprising administering to the individual a composition comprising a plant phenol, wherein the composition comprises a plant extract selected from the group consisting of extracts from thyme, pomegranate, green coffee, and mixtures thereof, and the plant extract provides at least a portion of the plant phenol.

4. The method of claim 1, wherein the composition is administered orally.

5. The method of claim 1, wherein the composition is administered topical-orally.

6. The method of claim 1, wherein the composition is administered in the form of a spray.

7. The method of claim 1, wherein the individual is a human or a pet animal.

8. The method of claim 1, wherein the individual is selected from the group consisting of a young child between the age of 1 month and six years, an older child between the age of 6 to 18 years, and an adult person.

9. The method of claim 1, wherein the composition is selected from the group consisting of a nutritional composition, an oral nutritional supplement and a pharmaceutical product.

10. The method of claim 1, wherein the composition is selected from the group consisting of an infant feeding composition, an amino acid based beverage or formula, a follow-up formula, a growing-up milk, an infant cereal, and a baby nutritional composition.

11. The method of claim 1, wherein the composition is selected from the group consisting of a beverage product, a yoghurt product, fermented milk, a fruit juice, a dried powder in a sachet, and a cereal bar.

12. The method of claim 1, wherein the composition is a food for a specific medical purpose.

13. A method for treatment of eosinophilic esophagitis in an individual in need thereof, the method comprising administering to the individual a composition comprising a plant phenol, wherein the composition comprises two plant extracts that provide at least a portion of the plant phenols, and the two plant extracts are selected from the group consisting of thyme, pomegranate, green coffee, and mixtures thereof.

14. The method of claim 1, wherein the composition is administered to the individual in a dose of 10 to 50 mg of the plant phenol/kg of body weight per day.

15. The method of claim 1, wherein the composition is administered to the individual in a dose that provides 25 mg to 10 g of the plant phenol per day.

16. The method of claim 1, wherein the composition comprises at least one additional ingredient selected from the group consisting of amino acids, a fat and a carbohydrate.

17. The method of claim 1, wherein the composition further comprises a vitamin selected from the group consisting of Vitamin A, Vitamin E, Vitamin C, Vitamin B1, Vitamin B2, Pantothenic Acid, Vitamin B6, Vitamin B12, Niacin, Folic Acid, Biotin, Choline, and combinations thereof.

18. A method for treatment of eosinophilic esophagitis in an individual in need thereof, the method comprising administering to the individual a composition comprising a plant phenol, for at least 120 days, wherein the plant phenol is selected from the group consisting of rosmarinic acid, ellagic acid, chlorogenic acid, and mixtures thereof.

* * * * *